(12) United States Patent
Lee et al.

(10) Patent No.: US 10,252,993 B2
(45) Date of Patent: Apr. 9, 2019

(54) CRYSTALLINE FORM OF ATORVASTATIN HEMI-CALCIUM SALT, HYDRATE THEREOF, AND METHOD OF PRODUCING THE SAME

(71) Applicant: KYONGBO PHARM, Asan-si (KR)

(72) Inventors: Kyung Ju Lee, Cheonan-si (KR); Hoe Joo Son, Suwon-Si (KR); Doo Seong Choi, Yongin-si (KR); Sun Ho Chang, Asan-si (KR); Do Yeon Oh, Asan-Si (KR)

(73) Assignee: KYONGBO PHARM, Asan-si (KR)

( * ) Notice: Subject to any disclaimer, the term of this patent is extended or adjusted under 35 U.S.C. 154(b) by 0 days.

(21) Appl. No.: 15/441,430

(22) Filed: Feb. 24, 2017

(65) Prior Publication Data

US 2018/0009747 A1 Jan. 11, 2018

Related U.S. Application Data

(60) Continuation of application No. 14/106,200, filed on Dec. 13, 2013, now abandoned, which is a continuation of application No. 13/360,034, filed on Jan. 27, 2012, now abandoned, which is a division of application No. 13/012,385, filed on Jan. 24, 2011, now abandoned.

(30) Foreign Application Priority Data

Jul. 28, 2010 (KR) .................. 10-2010-0072991

(51) Int. Cl.
C07D 207/34 (2006.01)

(52) U.S. Cl.
CPC .................. *C07D 207/34* (2013.01)

(58) Field of Classification Search
CPC .................................................. C07D 207/34
See application file for complete search history.

(56) References Cited

U.S. PATENT DOCUMENTS

| | | | |
|---|---|---|---|
| 4,681,893 A | 7/1987 | Roth |
| 5,003,080 A | 3/1991 | Butler et al. |
| 5,097,045 A | 3/1992 | Butler et al. |
| 5,124,482 A | 6/1992 | Butler et al. |
| 5,149,837 A | 9/1992 | Butler et al. |
| 5,155,251 A | 10/1992 | Butler et al. |
| 5,216,174 A | 6/1993 | Butler et al. |
| 5,245,047 A | 9/1993 | Butler et al. |
| 5,273,995 A | 12/1993 | Roth |
| 5,342,952 A | 8/1994 | Butler et al. |
| 5,397,792 A | 3/1995 | Butler et al. |
| 5,969,156 A | 10/1999 | Briggs et al. |
| 6,121,461 A | 9/2000 | McKenzie |

FOREIGN PATENT DOCUMENTS

| | | |
|---|---|---|
| CN | 101492406 A | 7/2009 |
| EP | 1 424 324 A1 | 6/2004 |
| KR | 10-2008_0070951 | 8/2008 |
| KR | 10-2009-0056527 | 6/2009 |
| KR | 10-2009-0090942 | 8/2009 |
| KR | 10-2009-0104253 | 10/2009 |
| WO | 97/03958 A1 | 2/1997 |
| WO | 97/03959 A1 | 2/1997 |
| WO | 01/36384 A1 | 5/2001 |
| WO | 02/41834 A2 | 5/2002 |
| WO | 02/43732 A1 | 6/2002 |
| WO | 02/051804 A1 | 7/2002 |
| WO | 02/072073 A2 | 9/2002 |
| WO | 03/004470 A1 | 1/2003 |
| WO | 03/011826 A1 | 2/2003 |
| WO | 03/050085 A1 | 6/2003 |
| WO | 03/070665 A2 | 8/2003 |
| WO | 03/070702 A1 | 8/2003 |
| WO | 04/043918 A1 | 5/2004 |

(Continued)

OTHER PUBLICATIONS

Brittain (Polymorphism in Pharmaceutical Solids, vol. 95, 1999, Taylor & Francs, Harry G. Brittain (Ed.), 427 pp.).

(Continued)

*Primary Examiner* — Robert H Havlin
(74) *Attorney, Agent, or Firm* — Heslin Rothenberg Farley & Mesiti, P.C.; Philip Hansen

(57) ABSTRACT

The present invention provides a novel crystalline form of [R—(R*,R*)]-2-(4-fluorophenyl)-β,δ-dihydroxy-5-(1-methylethyl)-3-phenyl-4-[(phenylamino)carbonyl]-1H-pyrrol-1-heptanoic acid hemi-calcium salt (atorvastatin hemi-calcium salt) of the following formula 1, which is known to be useful as a drug, a hydrate thereof and a preparation method thereof:

[Formula 1]

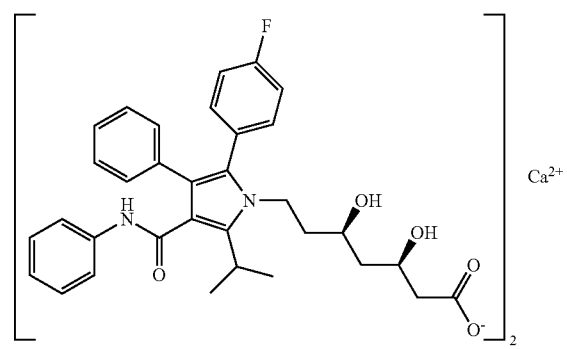

1 Claim, 9 Drawing Sheets

(56) References Cited

FOREIGN PATENT DOCUMENTS

| WO | 2005/026116 A1 | 3/2005 |
| WO | 2006/011041 A2 | 2/2006 |
| WO | 2006/012499 A2 | 2/2006 |
| WO | 2006/048894 A1 | 5/2006 |
| WO | 2006/106372 A1 | 10/2006 |
| WO | 2007/020421 A1 | 2/2007 |
| WO | 2007/058664 A1 | 5/2007 |
| WO | 2007/070667 A2 | 6/2007 |
| WO | 2007/096903 A2 | 8/2007 |
| WO | 2007/099552 A2 | 9/2007 |
| WO | 2007/103223 A1 | 9/2007 |
| WO | 2007/118873 A2 | 10/2007 |
| WO | 2007/133597 A1 | 11/2007 |
| WO | 2008/02655 A2 | 1/2008 |
| WO | 2008/053495 A1 | 5/2008 |
| WO | 2008/108572 A1 | 9/2008 |
| WO | 2009/007856 A2 | 1/2009 |

OTHER PUBLICATIONS

Caira, Mino R., Crystalline Polymorphism of Organic Compounds, Topics in Current Chemistry, 1998, vol. 198, pp. 163-208.
Campbell Roberts et al., J. Pharm. Biomed. Anal., 28 (2002) 1149-59.
Chen et al., J. Pharm. Sci., (1999), v. 88, p. 1191-1200.
Hurst et al., Analytica Chimica Acta, 337 (1997), 233-52.
Jin, Yong Suk et al., New Crystalline Solvates of Atorvastatin Calcium, Chemical Engineering Technology, 2010, vol. 33, No. 5, pp. 839-844.
Misture et al., Encyclopedia of Materials: Science and Technology (2001) pp. 9799-9809 [1-10].
Morissette et al. (Advanced Drug Delivery Reviews 56 (2004) 275-300).
Tian et al., European Journal of Pharmaceutics and Biopharmaceutics 66 (2007) 466-474.
Tiwari et al., J. Pharm. Biomed. Anal., 43 (2007) 865-72.
U.S. Pharmacopia #23, National Formulary #18 (1995), p. 1843-1844.

CRYSTALLINE FORM OF ATORVASTATIN HEMI-CALCIUM SALT, HYDRATE THEREOF, AND METHOD OF PRODUCING THE SAME

CROSS REFERENCE TO RELATED APPLICATION

This application is a non-provisional application, which claims priority to Korean Application No. 10-2010-0072991, filed Jul. 28, 2010. The entire content of the prior application is hereby incorporated by reference.

TECHNICAL FIELD

The present invention relates to a novel crystal form of atorvastatin hemi-calcium salt, a hydrate thereof, a preparation method thereof, and a pharmaceutical composition containing the same.

BACKGROUND ART

Atorvastatin having the following structural formula is an inhibitor of HMG-CoA reductase (3-hydroxy-3-methylglutaryl-coenzyme A reductase) and is known as an effective therapeutic agent for hyperlipidemia, hypercholesterolemia, arteriosclerosis, osteoporosis, benign prostatic hyperplasia and Alzheimer's disease:

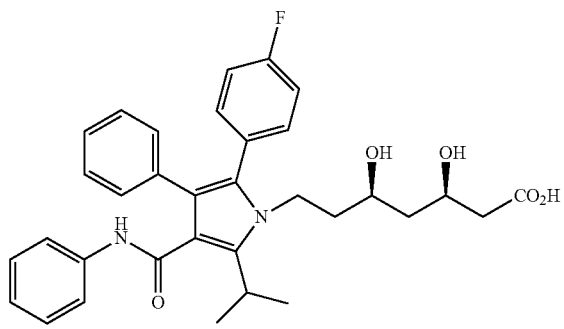 [SMILES: CC(C)c1c(C(=O)Nc2ccccc2)c(-c2ccccc2)c(-c2ccc(F)cc2)n1CC[C@@H](O)C[C@@H](O)CC(=O)O]

U.S. Pat. Nos. 4,681,893 and 5,273,995 discloses, as atorvastatin, lactone forms of trans (±)-5-(4-fluorophenyl)-2-(1-methylethyl)-N,4-diphenyl-1-[(2-tetrahydro-4-hydroxy-6-oxo-2H-pyran-2-yl)ethyl]-1H-pyrrole-3-carboxamide, and amorphous forms of [R—(R*,R*)]-2-(4-fluorophenyl)-β,δ-dihydroxy-5-(1-methylethyl)-3-phenyl-4-[(phenylamino)carbonyl]-1H-pyrrole-1-heptanoic acid and its calcium salts.

Various methods for preparing atorvastatin and methods for preparing an important intermediate of atorvastatin are disclosed in U.S. Pat. Nos. 5,003,080, 5,097,045, 5,124,482, 5,149,837, 5,155,251, 5,216,174, 5,245,047, 5,273,995, 5,397,792 and 5,342,952. Such amorphous forms are unstable to heat, light, oxygen and moisture, and thus the storage conditions thereof are limited. Also, such amorphous forms are unsuitable for the filtration and drying of products in mass production.

The crystalline polymorphic form of atorvastatin hemi-calcium salt is disclosed in U.S. Pat. Nos. 5,969,156 and 6,121,461 and International Patent Publication Nos. WO 01/36384, WO 02/43732, WO 03/070702 and WO 03/004470.

The atorvastatin hemi-calcium salt may be formulated into forms for oral administration, such as tablets, capsules, lozenges and powders. Thus, there is a need to produce atorvastatin in a pure and crystalline form to enable formulations to meet exacting pharmaceutical requirements and specifications. Accordingly, a crystalline form of atorvastatin that is more stable and easy to produce in large amounts is required in the art.

PRIOR-ART DOCUMENTS (Patent Document 1) U.S. Pat. No. 5,969,156
(Patent Document 2) U.S. Pat. No. 6,121,461

DISCLOSURE

Technical Problem

A crystalline form I in U.S. Pat. No. 5,969,156 is obtained by crystallization at a high temperature of 47~52 □ in an aqueous solution containing 10-15% methanol, and this crystallization causes an increase in the related impurities of atorvastatin during the process. A method of adding a seed crystal and a method of carrying out filtration at reduced temperature after carrying out a reaction at high temperature cause a decrease in the productivity in mass production.

A crystalline form II is obtained by stirring the solid in methanol containing 40-50% water for 3 days, and a crystalline form IV is obtained by stirring the obtained crystalline form I at high temperature in a methanol solvent and is considered to be inefficient for mass production.

A crystalline form III in U.S. Pat. No. 6,121,461 is obtained by exposing atorvastatin to a high relative humidity for 11 days and is also considered to be unsuitable for mass production.

Many documents relating to methods for preparing atorvastatin hemi-calcium salt are known, and the kinds and contents of impurities that can be included in crude atorvastatin hemi-calcium salt vary depending on the preparation method. In Warner-Lambert Company (Pfizer) who has originally developed the atorvastatin hemi-calcium salt, four major impurities of the following formulas 2a, 2b, 2c and 2d are managed (recorded in Lipitor Interview Form, Japanese Medicine Prescription):

[Formula 2a]

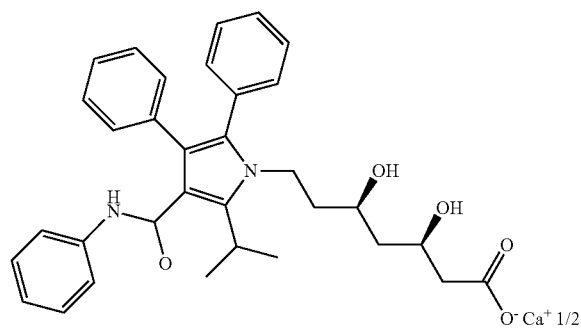

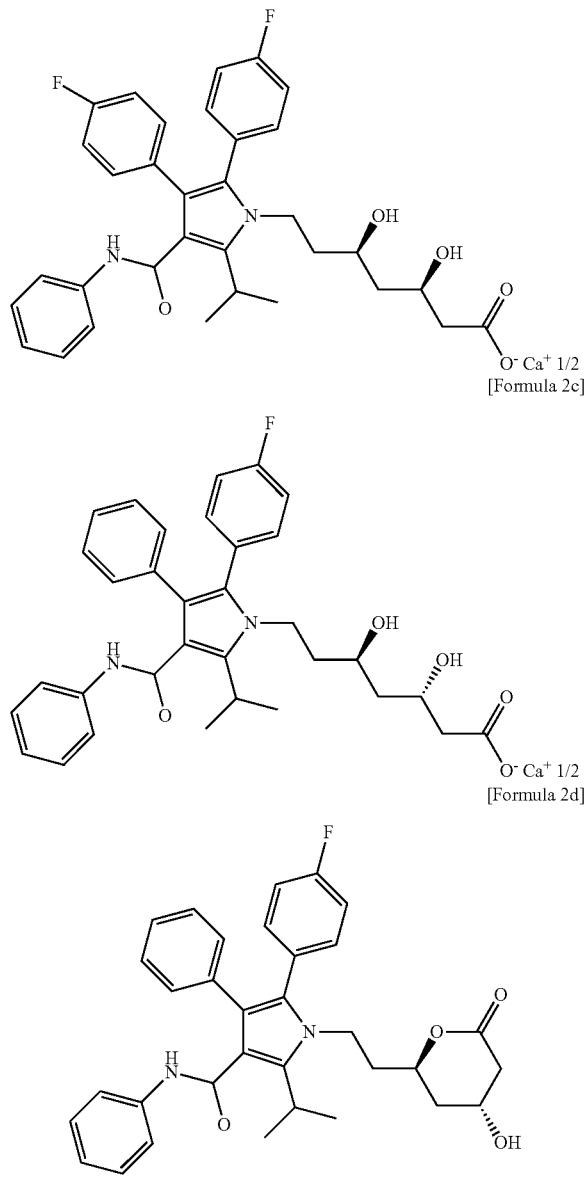

[Formula 2b]

[Formula 2c]

[Formula 2d]

Among the impurities des-fluoro form (2a), difluoro form (2b), trans-isomer form (2c) and lactone form (2d), the lactone form that is a stability-related impurity is particularly sensitive to temperature, and thus increases when it is stored for a long period of time or at high temperature.

Either stirring at high temperature or stirring and exposure for a long period of time, like the method for preparing the crystalline form I in U.S. Pat. No. 5,969,156, cause an increase in the impurity in a reaction solution. Due to this problem, it is important to minutely manage the impurity during the preparation of atorvastatin hemi-calcium salt.

Technical Solution

Accordingly, the present inventors have conducted many studies and, as a result, have developed a novel crystalline form of high-purity, uniform atorvastatin hemi-calcium salt of the following formula 1, which is more stable, easy to produce in large amounts and show no difference between batches according to the preparation method:

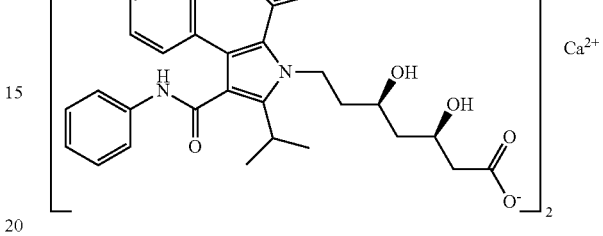

[Formula 1]

In the specification, the novel crystalline form developed by the present inventors, which has a characteristic X-ray powder diffraction spectrum and can be advantageously used in a pharmaceutical composition due to its excellent chemical stability, was named "Form α atorvastatin hemi-calcium salt".

Also, unless otherwise defined herein, the term "crude atorvastatin hemi-calcium salt" has the same meaning as "amorphous atorvastatin hemi-calcium salt" or an amorphous form of atorvastatin hemi-calcium salt".

The present invention provides an Form α atorvastatin hemi-calcium salt which has broad peaks having a relative intensity greater than 20% at 2θ values of about 8.8, 9.6, 16.9, 21.7 and 23.5±0.2° in an X-ray powder diffraction measured using CuKα radiation.

The Form α atorvastatin hemi-calcium salt of the present invention is characterized by having peaks having a relative intensity greater than 10% at 2θ values of about 8.8, 9.6, 11.9, 16.9, 19.6, 21.7, 23.5 and 29.7±0.5° in an X-ray powder diffraction measured using CuKα radiation. More specifically, the Form α atorvastatin hemi-calcium salt of the present invention has the X-ray powder diffraction data shown in the following Table:

| 2θ | d | Relative intensity (>10%) |
|---|---|---|
| 8.820 | 10.0175 | 31.1 |
| 9.642 | 9.1652 | 24.4 |
| 11.860 | 7.4562 | 13.1 |
| 16.900 | 5.242 | 100.0 |
| 19.583 | 4.5294 | 16.9 |
| 21.679 | 4.0960 | 44.1 |
| 23.480 | 3.7858 | 26.6 |
| 29.702 | 3.0054 | 15.9 |

The X-ray powder diffraction spectrum can be obtained using a RIKAGU X-ray powder diffractometer with Cu radiation of λ=1.54059 A in the 2θ range of 3~50°.

Also, the $^{13}$C NMR (nuclear magnetic resonance) spectrum of the Form α atorvastatin hemi-calcium salt of the present invention shows the characteristics shown in the following Table.

The $^{13}$C NMR spectrum was measured using a 500 MHz Solid NMR spectrometer Advance☐ 500WB (Bruker).

| Chemical shift |
|---|
| 224.37 |
| 224.15 |
| 221.60 |
| 217.76 |
| 216.11 |
| 214.64 |
| 214.43 |
| 210.16 |
| 181.68 |
| 180.17 |
| 179.27 |
| 177.60 |
| 165.92 |
| 161.45 |
| 159.48 |
| 136.75 |
| 134.15 |
| 130.25 |
| 128.63 |
| 127.02 |
| 122.68 |
| 120.73 |
| 120.03 |
| 117.34 |
| 113.94 |
| 112.90 |
| 74.01 |
| 72.13 |
| 70.83 |
| 69.46 |
| 68.32 |
| 67.12 |
| 66.41 |
| 64.88 |
| 64.01 |
| 49.26 |
| 47.69 |
| 46.45 |
| 45.84 |
| 45.28 |
| 44.57 |
| 42.32 |
| 40.72 |
| 39.38 |
| 36.84 |
| 35.16 |
| 25.43 |
| 23.85 |
| 20.24 |
| 18.52 |

The present invention provides a crystalline Form α atorvastatin hemi-calcium salt hydrate. The crystalline Form α atorvastatin hemi-calcium salt hydrate contains 1-3 moles of water per mole of salt. Most preferably, it contains 2-3 moles of water.

According to the present invention, there is provided a high-purity, crystalline Form α atorvastatin hemi-calcium salt, which is prepared by crystallizing stably within a short time at room temperature with low calorie consumption, is inexpensive, eliminates unnecessary processes increasing an impurity and is stable under storage conditions.

The crude atorvastatin that is used in the present invention may be an atorvastatin hemi-calcium salt synthesized according to the method of U.S. Pat. No. 5,273,995, or the amorphous form of or a mixture of amorphous and crystalline forms of atorvastatin hemi-calcium salt prepared according to the preparation method of Korean Patent Registration No. 10-0881617.

According to the present invention, a high-purity, crystalline Form α atorvastain hemi-calcium salt can be obtained in which the HPLC area ratio of formula 2d, which is an impurity, is less than 0.11% and the HPLC area ratio of atorvastatin hemi-calcium salt is more than 99.6% and which has a purity of more than 99.9%.

Also, the present invention provides a method for preparing an Form α atorvastatin hemi-calcium salt or a hydrate thereof, comprising suspending a crude atorvastatin hemi-calcium salt in a mixed solvent of methanol and water, and stirring the suspension.

In the preparation method of the present invention, the volume ratio of methanol:water in the mixed solvent is preferably 1:10 (v/v)~1:15 (v/v), and most preferably 1:12 (v/v).

In the preparation method of the present invention, the ratio of volume of mixed solvent:weight of crude atorvastatin hemi-calcium salt is preferably 1:40~80 (v/wt), and more preferably 1:60~65 (v/wt).

In the preparation method of the present invention, the reaction is preferably carried out at a temperature of 5~25 □, and most preferably 10~20 □.

In the preparation method of the present invention, the reaction is preferably carried out for 1-10 hours, and most preferably 1-5 hours.

Advantageous Effects

The crystalline Form α atorvastatin hemi-calcium salt according to the present invention is an inhibitor of HMG-CoA reductase and is useful as a therapeutic agent for hyperlipidemia, hypercholesterolemia, osteoporosis and Alzheimer's disease.

BEST MODE FOR CARRYING OUT THE INVENTION

Hereinafter, the present invention will be described in further detail with reference to examples. It is to be understood, however, that these examples are for illustrative purposes only and the scope of the present invention is not limited thereto.

EXAMPLE 1

Figure 1:
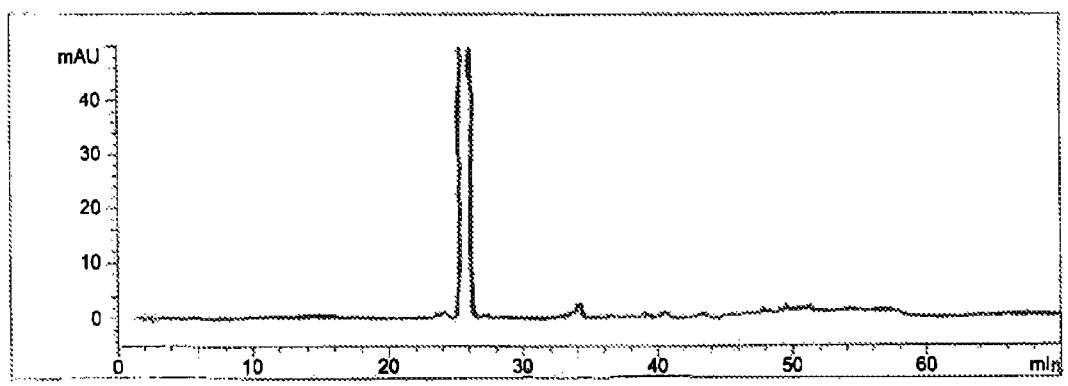
FIG. 1 shows the results of high-performance liquid chromatography (HPLC) of an amorphous atorvastatin hemi-calcium salt prepared according to the method of Example 10 of U.S. Pat. No. 5,273,995.

As crude atorvastatin, an amorphous atorvastatin hemi-calcium salt prepared according to the method of Example 10 of U.S. Pat. No. 5,273,995 was used. The HPLC graph and peak results of the amorphous atorvastatin hemi-calcium salt are shown in FIG. 1 and Table 1 below.

TABLE 1

|   | Classification | RT | Area | % area |
|---|---|---|---|---|
| 1 | Peak 1 | 15.296 | 2.48858 | 0.006 |
| 2 | Peak 2 | 16.333 | 1.71720 | 0.004 |
| 3 | des-fluoro | 23.616 | 21.17357 | 0.055 |
| 4 | trans-isomer | 24.143 | 30.46073 | 0.079 |
| 5 | Atorvastatin | 25.723 | 38294.5 | 99.457 |
| 6 | di-fluoro | 27.293 | 7.37744 | 0.019 |
| 7 | Peak 7 | 32.645 | 0.00000 | 0.000 |
| 8 | Lactone | 34.209 | 63.30801 | 0.164 |
| 9 | Peak 9 | 39.358 | 12.00771 | 0.031 |
| 10 | Pak 10 | 40.697 | 26.27836 | 0.068 |
| 11 | Peak 11 | 47.803 | 21.32455 | 0.055 |
| 12 | Peak 12 | 49.506 | 18.76946 | 0.049 |
| 13 | Peak 13 | 51.266 | 4.14277 | 0.011 |

Subsequently, 10 g of the prepared amorphous atorvastatin hemi-calcium salt was added to a mixture of 50 ml of methanol and 600 ml of water and stirred at room temperature for 1 hour. The stirred mixture was filtrated, and the resulting solid was washed with water. The washed solid was dried under reduced pressure at 40° C. for 5 hours, thus obtained 9.6 g of a crystalline Form α atorvastatin hemi-calcium salt.

Figure 2:
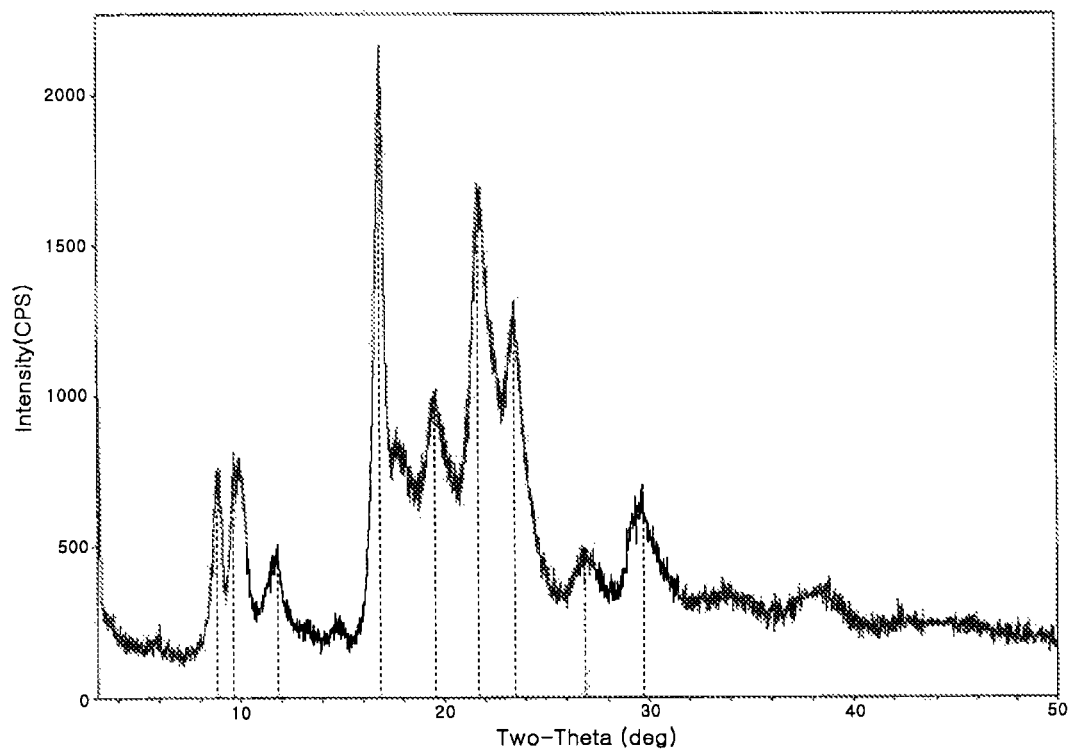
FIG. 2 shows the powder X-ray diffraction spectrum of a crystalline atorvastatin hemi-calcium salt prepared according to the method of Example 1 of present invention.

The X-ray powder diffraction spectrum of the obtained crystalline Form α atorvastatin hemi-calcium salt is shown in FIG. 2, and the numerical values of the X-ray powder diffraction spectrum are shown in Table 2 below.

TABLE 2

| 2θ | d | Relative intensity (>10%) |
|---|---|---|
| 8.820 | 10.0175 | 31.1 |
| 9.642 | 9.1652 | 24.4 |
| 11.860 | 7.4562 | 13.1 |
| 16.900 | 5.242 | 100.0 |
| 19.583 | 4.5294 | 16.9 |
| 21.679 | 4.0960 | 44.1 |
| 23.480 | 3.7858 | 26.6 |
| 29.702 | 3.0054 | 15.9 |

Figure 3:
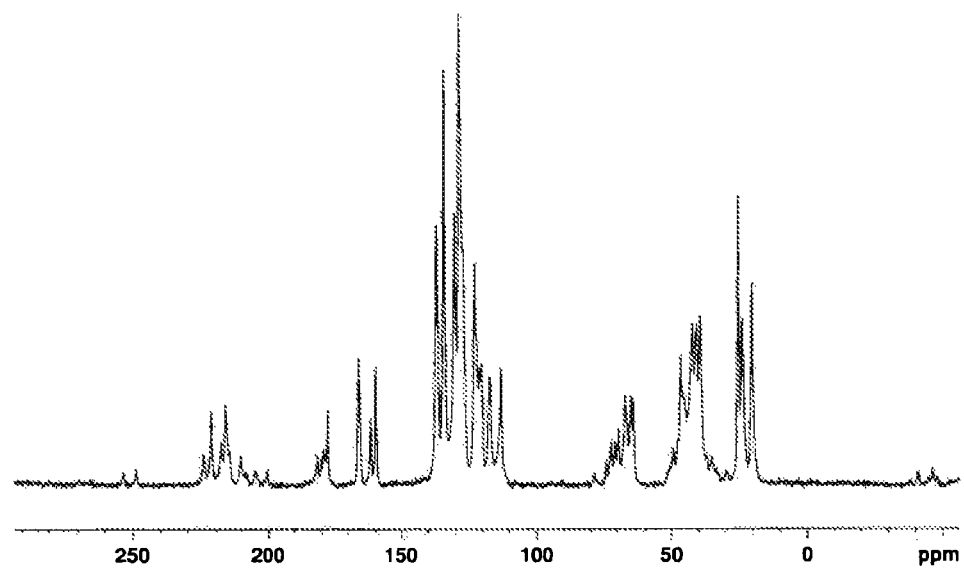
FIG. 3 shows the solid-state $^{13}C$ nuclear magnetic resonance (NMR) spectrum of the crystalline atorvastatin hemi-calcium salt prepared according to the method of Example 1 of present invention.

The $^{13}$C nuclear magnetic resonance (NMR) spectrum of the obtained crystalline Form α atorvastatin hemi-calcium salt is shown in FIG. 3, and the numerical values of the $^{13}$C NMR spectrum are shown in Table 3.

TABLE 3

| Chemical shift |
|---|
| 224.37 |
| 224.15 |
| 221.60 |
| 217.76 |
| 216.11 |
| 214.64 |
| 214.43 |
| 210.16 |
| 181.68 |
| 180.17 |
| 179.27 |
| 177.60 |
| 165.92 |
| 161.45 |
| 159.48 |
| 136.75 |
| 134.15 |
| 130.25 |
| 128.63 |
| 127.02 |
| 122.68 |
| 120.73 |
| 120.03 |
| 117.34 |
| 113.94 |
| 112.90 |
| 74.01 |
| 72.13 |
| 70.83 |
| 69.46 |
| 68.32 |
| 67.12 |
| 66.41 |
| 64.88 |
| 64.01 |
| 49.26 |
| 47.69 |
| 46.45 |
| 45.84 |
| 45.28 |
| 44.57 |
| 42.32 |
| 40.72 |
| 39.38 |
| 36.84 |
| 35.16 |
| 25.43 |
| 23.85 |
| 20.24 |
| 18.52 |

Figure 4:
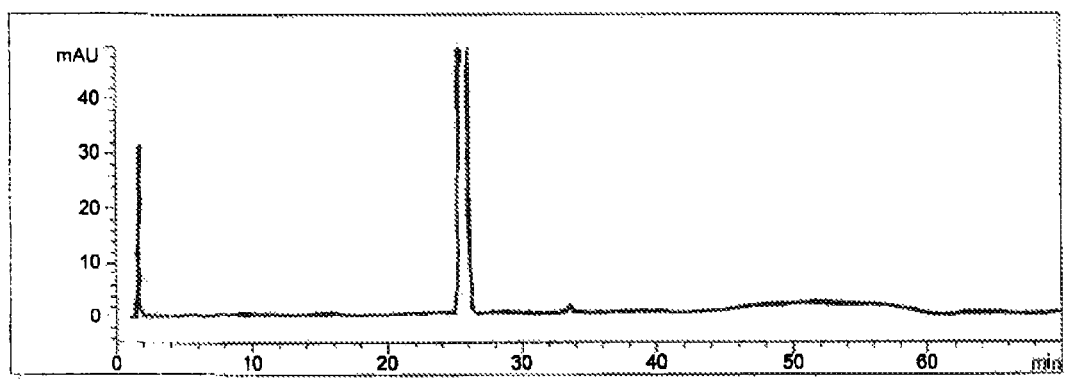
FIG. 4 shows the results of HPLC of a reaction product obtained before filtration of the mixture in the method of Example 1 of the present invention.
Figure 5:
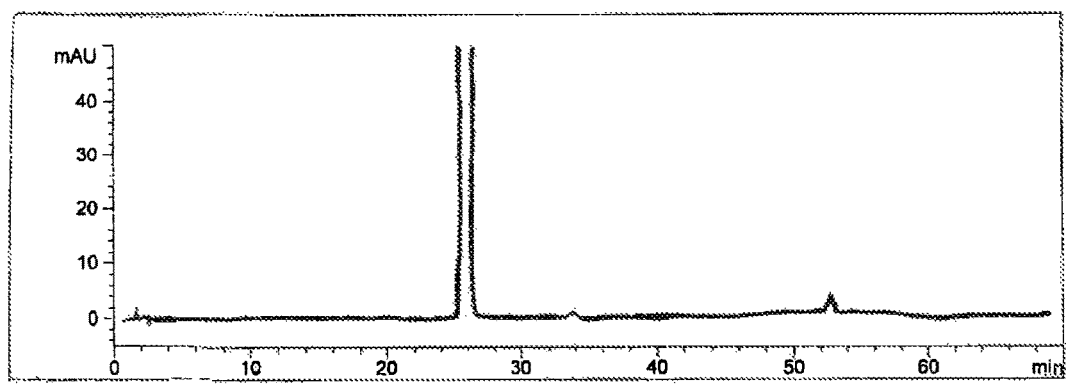
FIG. 5 shows the results of HPLC of a crystalline atorvastatin hemi-calcium salt obtained by filtering, water washing and drying the reaction product in the method of Example 1 of the present invention.

After the mixture of methanol, water and atorvastatin has been stirred, the resulting reaction product was taken with a pipette before filtration and subjected to HPLC. The HPLC results of the reaction product are shown in FIG. 4 and Table 4 below. The HPLC graph and peak results of the crystalline Form α atorvastatin hemi-calcium salt that has been filtered, washed with water and dried are shown in FIG. 5 and Table 5 below.

TABLE 4

|   | Classification | RT | Area | % area |
|---|---|---|---|---|
| 1 | Peak 1 | 15.472 | 17.91986 | 0.061 |
| 2 | Peak 2 | 16.336 | 9.32039 | 0.032 |
| 3 | des-fluoro | 23.552 | 16.81358 | 0.057 |
| 4 | trans-isomer | 24.094 | 23.46393 | 0.080 |
| 5 | Atorvastatin | 25.655 | 29329.1 | 99.52 |
| 6 | di-fluoro | 27.177 | 3.40998 | 0.012 |

TABLE 4-continued

|  | Classification | RT | Area | % area |
|---|---|---|---|---|
| 7 | Peak 7 | 32.564 | 2.16635 | 0.007 |
| 8 | lactone | 33.596 | 48.39322 | 0.165 |
| 9 | Peak 9 | 39.160 | 3.17732 | 0.011 |
| 10 | Peak 10 | 41.657 | 4.58379 | 0.016 |
| 11 | Peak 11 | 47.817 | 8.68831 | 0.029 |
| 12 | Peak 12 | 49.015 | 4.54222 | 0.015 |

TABLE 5

|  | Classification | RT | Area | % area |
|---|---|---|---|---|
| 1 | Peak 1 | 15.398 | 1.47642 | 0.004 |
| 2 | Peak 2 | 17.078 | 3.99462 | 0.010 |
| 3 | des-fluoro | 23.764 | 22.21842 | 0.055 |
| 4 | trans-isomer | 24.331 | 20.21887 | 0.050 |
| 5 | Atorvastatin | 25.881 | 40320.8 | 99.65 |
| 6 | di-fluoro | 27.461 | 3.47598 | 0.009 |
| 7 | Peak 7 | 32.614 | 14.46725 | 0.036 |
| 8 | lactone | 33.868 | 44.04422 | 0.109 |
| 9 | Peak 9 | 39.574 | 7.35996 | 0.018 |
| 10 | Peak 10 | 40.879 | 9.01929 | 0.022 |
| 11 | Peak 11 | 47.552 | 8.38994 | 0.021 |
| 12 | Peak 12 | 49.894 | 7.57033 | 0.019 |

As can be seen in Tables above, the % area of the impurity of lactone form was 0.164% in the crude atorvastatin hemi-calcium salt (Table 1), was maintained at 0.165% before filtration of the mixture (Table 4), and was 0.109% after filtration of the mixture (Table 5). This suggests that the reaction mixture shows a stable state which does not increase the impurity.

COMPARATIVE EXAMPLE 1

For comparison with the present invention, a crystalline form I was prepared in the following manner according to method B of Example 1 of U.S. Pat. No. 5,969,156, and the HPLC area ratio of the crystalline form I atorvastatin trihydrate was examined.

10 g of amorphous atorvastatin was stirred in a mixture of 170 ml of water and 30 ml of methanol at 40° C. for 17 hours. The mixture was filtered and washed with water. Then, the resulting solid was dried under reduced pressure, thus obtaining 9.6 g of a crystalline form I atorvastatin hemi-calcium salt.

Figure 6:
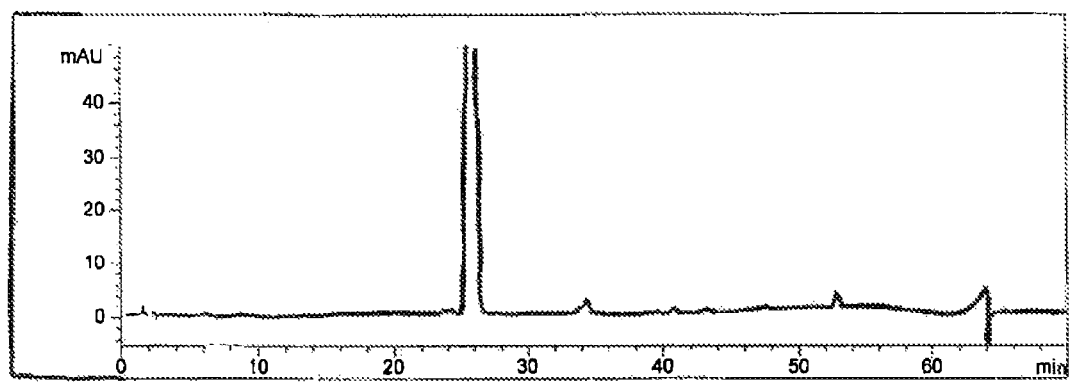
FIG. 6 shows the results of HPLC of a reaction product obtained before filtration of the mixture in the method of Comparative Example 1.
Figure 7:
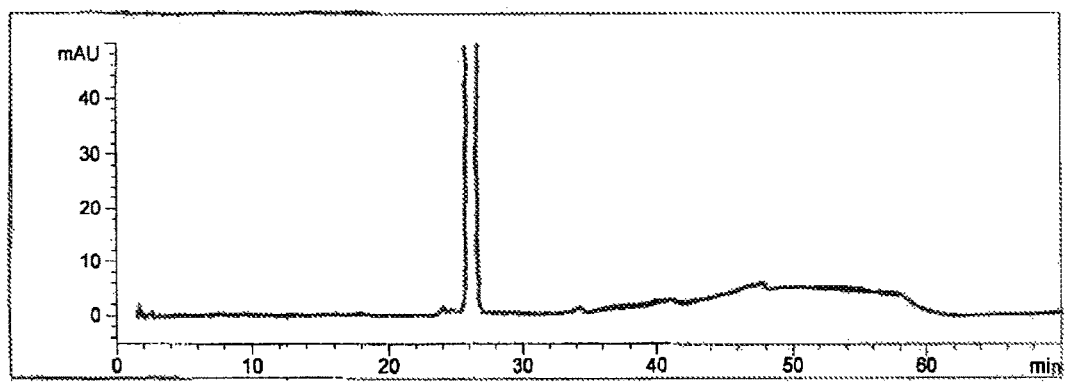
FIG. 7 shows the results of HPLC of a crystalline form I atorvastatin hemi-calcium salt obtained by filtering, water washing and drying the reaction product in the method of Comparative Example 1.

After the mixture of methanol, water and atorvastatin has been stirred, the resulting reaction product was taken with a pipette before filtration and subjected to HPLC. The results of HPLC of the reaction product are shown in FIG. 6 and Table 6 below. The HPLC graph and peak results of the crystalline form I atorvastatin hemi-calcium salt that has been filtered, washed with water and dried are shown in FIG. 7 and Table 7 below.

TABLE 6

|  | Classification | RT | Area | % area |
|---|---|---|---|---|
| 1 | Peak 1 | 15.408 | 2.04671 | 0.005 |
| 2 | Peak 2 | 16.381 | 2.16140 | 0.006 |
| 3 | des-fluoro | 23.666 | 21.93967 | 0.057 |
| 4 | trans-isomer | 24.192 | 34.10612 | 0.089 |
| 5 | Atorvastatin | 25.777 | 38190.7 | 99.28 |
| 6 | di-fluoro | 27.344 | 6.60240 | 0.017 |

TABLE 6-continued

|  | Classification | RT | Area | % area |
|---|---|---|---|---|
| 7 | Peak 7 | 32.594 | 1.27799 | 0.003 |
| 8 | lactone | 34.277 | 124.41223 | 0.323 |
| 9 | Peak 9 | 39.421 | 13.85361 | 0.036 |
| 10 | Peak 10 | 40.771 | 31.64594 | 0.082 |
| 11 | Peak 11 | 47.517 | 20.25181 | 0.053 |
| 12 | Peak 12 | 49.321 | 18.38314 | 0.048 |

TABLE 7

|  | Classification | RT | Area | % area |
|---|---|---|---|---|
| 1 | Peak 1 | 15.591 | 17.33613 | 0.044 |
| 2 | Peak 2 | 16.637 | 2.97883 | 0.007 |
| 3 | des-fluoro | 23.978 | 21.56549 | 0.055 |
| 4 | trans-isomer | 24.841 | 22.55341 | 0.057 |
| 5 | Atorvastatin | 26.114 | 39301.8 | 99.40 |
| 6 | di-fluoro | 27.725 | 9.04092 | 0.023 |
| 7 | Peak 7 | 32.645 | 10.38568 | 0.026 |
| 8 | lactone | 34.238 | 52.05996 | 0.132 |
| 9 | Peak 9 | 39.857 | 16.09881 | 0.041 |
| 10 | Peak 10 | 41.204 | 33.47954 | 0.085 |
| 11 | Peak 11 | 47.687 | 32.49892 | 0.082 |
| 12 | Peak 12 | 49.440 | 18.34163 | 0.046 |

As can be seen in Tables above, the % area of the lactone impurity was 0.164% in the crude atorvastatin hemi-calcium salt (Table 1), but increased to 0.323% before filtration of the mixture (Table 6) and was shown to be 0.132% even after the mixture was filtered and then dried so that the impurity was removed to the parent liquor (Table 7).

This suggests that the impurity increases because the mixture is allowed to react at high temperature for 17 hours.

EXAMPLE 2

10 g of a mixture of amorphous and crystalline forms of atorvastatin hemi-calcium salt was added to a mixture of 50 ml of methanol and 500 ml of water and stirred at 5~15° C. for 5 hours. The stirred mixture was filtered and the resulting solid was washed with water. The washed solid was dried under reduced pressure at 40° C. for 5 hours, thus obtaining 9.8 g of a crystalline Form α atorvastatin hemi-calcium salt.

Figure 8:
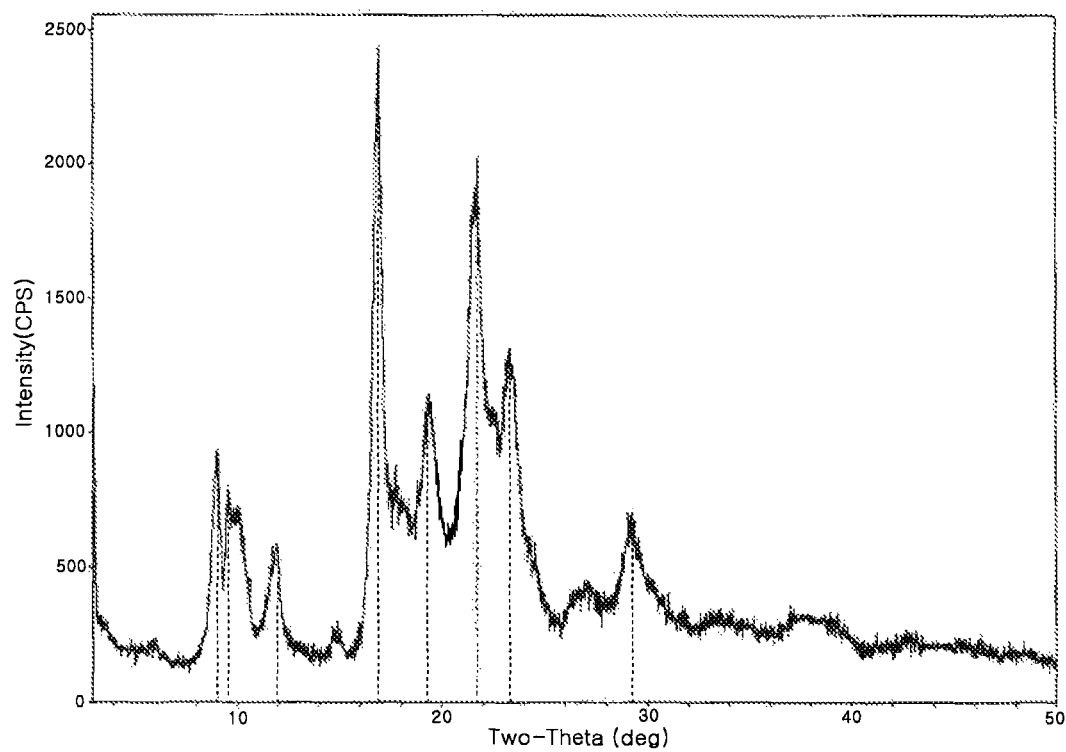
FIG. 8 shows the powder X-ray diffraction spectrum of a crystalline atorvastatin hemi-calcium salt prepared according to the method of Example 2 of present invention.

The X-ray powder diffraction spectrum of the obtained crystalline Form α atorvastatin hemi-calcium salt is shown in FIG. 8, and the numerical values of the X-ray powder diffraction spectrum are shown in Table 8 below.

Figure 9:
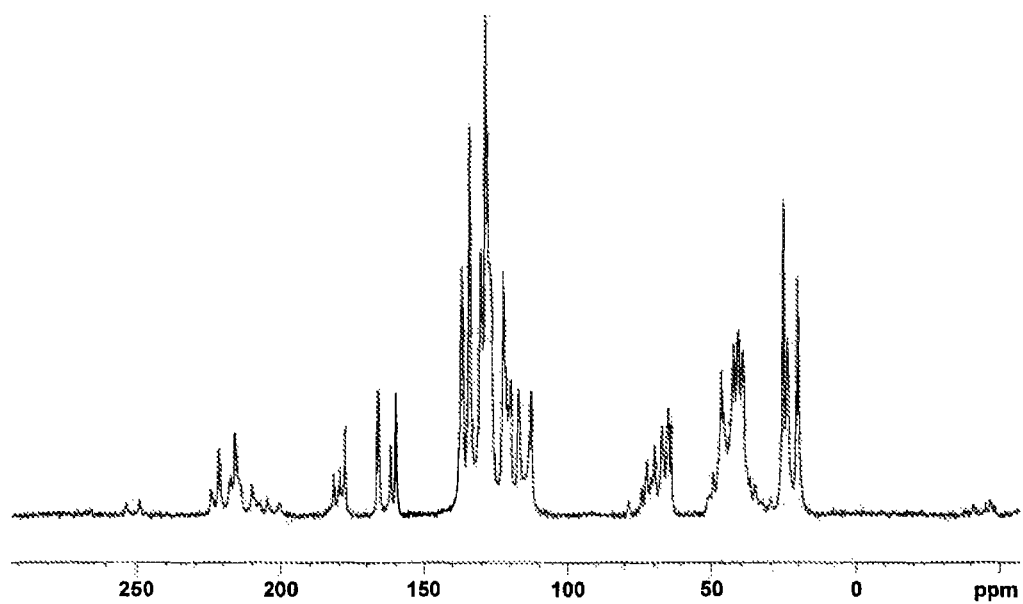
FIG. 9 shows the solid-state $^{13}$C nuclear magnetic resonance (NMR) spectrum of the crystalline atorvastatin hemi-calcium salt prepared according to the method of Example 2 of present invention.

The $^{13}C$ NMR (nuclear magnetic resonance) of the obtained crystalline Form α atorvastatin hemi-calcium salt are shown in FIG. 9, and the numerical values thereof are shown in Table 9 below.

TABLE 8

| 2θ | d | Relative intensity (>10%) |
|---|---|---|
| 8.960 | 9.8611 | 34.0 |
| 9.499 | 9.3029 | 19.5 |

TABLE 8-continued

| 2θ | d | Relative intensity (>10%) |
|---|---|---|
| 11.939 | 7.4065 | 16.2 |
| 16.899 | 5.2422 | 100.0 |
| 19.322 | 4.5900 | 21.4 |
| 21.701 | 4.0920 | 49.0 |
| 23.339 | 3.8083 | 22.4 |
| 29.258 | 3.0500 | 13.5 |

TABLE 9

| Chemical shift |
|---|
| 224.37 |
| 221.58 |
| 217.72 |
| 217.22 |
| 216.09 |
| 214.86 |
| 210.11 |
| 181.75 |
| 179.45 |
| 177.56 |
| 165.98 |
| 161.43 |
| 159.47 |
| 136.73 |
| 134.12 |
| 130.22 |
| 129.71 |

TABLE 9-continued

| Chemical shift |
|---|
| 128.64 |
| 127.34 |
| 122.65 |
| 120.67 |
| 120.02 |
| 117.32 |
| 112.90 |
| 74.00 |
| 72.81 |
| 72.68 |
| 72.21 |
| 70.81 |
| 70.37 |
| 69.51 |
| 67.17 |
| 65.32 |
| 64.99 |
| 63.96 |
| 49.23 |
| 48.39 |
| 47.54 |
| 46.44 |
| 45.77 |

TABLE 9-continued

| Chemical shift |
|---|
| 45.03 |
| 44.21 |
| 42.34 |
| 40.82 |
| 39.38 |
| 38.03 |
| 37.01 |
| 35.26 |
| 25.43 |
| 24.00 |
| 20.29 |

COMPARATIVE EXAMPLE 2

In order to examine whether the crystalline Form α atorvastatin hemi-calcium salt prepared according to the method of Example of the present invention is stable under storage conditions for three batches, a stability test was performed under accelerated conditions of a temperature of 40° C. and a relative humidity of 75%. The storage stability of the crystalline Form α atorvastatin hemi-calcium salt was determined using the HPLC area ratio. The test results are shown in Table 10 below.

TABLE 10

| Period | | Test conditions | Initial | 1 month | 2 months | 3 months | 4 months | 5 months | 6 months |
|---|---|---|---|---|---|---|---|---|---|
| Batch No. | 1 | 40° C. and 75% RH | 99.64 | 99.60 | 99.56 | 99.53 | 99.50 | 99.48 | 99.45 |
| | 2 | 40° C. and 75% RH | 99.65 | 99.60 | 99.58 | 99.55 | 99.52 | 99.50 | 99.48 |
| | 3 | 40° C. and 75% RH | 99.70 | 99.66 | 99.60 | 99.57 | 99.54 | 99.51 | 99.48 |

As can be seen in Table 10 above, the purity of the crystalline Form α atorvastatin hemi-calcium salt was maintained without a significant change under accelerated conditions. Thus, it could be seen that the crystalline Form α atorvastatin hemi-calcium salt showed excellent stability.

The invention claimed is:

1. A method for preparing a crystalline Form α atorvastatin hemi-calcium salt, comprising the steps of:
   a) suspending a crude atorvastatin hemi-calcium salt in a mixed solvent of methanol and water, wherein the volume ratio of methanol:water in the mixed solvent is 1:10 (v/v)~1:15 (v/v); and
   b) stirring the suspension at a reaction temperature of 5~25° C. for 1-10 hours;
   wherein the crystalline Form α atorvastatin hemi-calcium salt has peaks having a relative intensity greater than 10% at 2θ values of 8.8, 9.6, 11.9, 16.9, 19.6, 21.7, 23.5, and 29.7 in the X-ray powder diffraction;
   wherein the method does not include adding a seed crystal.

* * * * *